(12) United States Patent
Hendrix et al.

(10) Patent No.: US 7,771,924 B2
(45) Date of Patent: Aug. 10, 2010

(54) METHODS FOR DETERMINING THE RELATIVE BENEFITS AND/OR EVALUATING QUANTITATIVE CHANGES OF PRODUCTS ON EPITHELIAL TISSUE

(75) Inventors: Stephen Worth Hendrix, Clarksville, OH (US); Scott Edward Osborne, Liberty, OH (US); Susan Baldwin, Cincinnati, OH (US)

(73) Assignee: The Procter & Gamble Company, Cincinnati, OH (US)

( * ) Notice: Subject to any disclaimer, the term of this patent is extended or adjusted under 35 U.S.C. 154(b) by 710 days.

(21) Appl. No.: 11/789,650

(22) Filed: Apr. 25, 2007

(65) Prior Publication Data

US 2007/0202490 A1 Aug. 30, 2007

Related U.S. Application Data

(62) Division of application No. 10/787,560, filed on Feb. 26, 2004, now Pat. No. 7,229,778.

(51) Int. Cl.
 *C12Q 1/00* (2006.01)
 *G01N 33/53* (2006.01)
 *G01N 33/567* (2006.01)
(52) U.S. Cl. .............................. 435/4; 435/7.1; 435/7.2
(58) Field of Classification Search ........................ None
See application file for complete search history.

(56) References Cited

U.S. PATENT DOCUMENTS

| | | |
|---|---|---|
| 5,675,517 A | 10/1997 | Stokdijk |
| 5,736,330 A | 4/1998 | Fulton |
| 5,981,180 A | 11/1999 | Chandler et al. |
| 6,046,807 A | 4/2000 | Chandler |
| 6,057,107 A | 5/2000 | Fulton |
| 6,139,800 A | 10/2000 | Chandler |
| 6,225,046 B1 | 5/2001 | Vesey et al. |
| 6,248,590 B1 | 6/2001 | Malachowski |
| 6,268,222 B1 | 7/2001 | Chandler et al. |
| 6,280,618 B2 | 8/2001 | Watkins et al. |
| 6,366,354 B1 | 4/2002 | Chandler |
| 6,382,228 B1 | 5/2002 | Cabuz et al. |
| 6,411,904 B1 | 6/2002 | Chandler |
| 6,449,562 B1 | 9/2002 | Chandler et al. |
| 6,514,295 B1 | 2/2003 | Chandler et al. |
| 6,524,793 B1 | 2/2003 | Chandler et al. |
| 6,528,165 B2 | 3/2003 | Chandler |
| 6,549,275 B1 | 4/2003 | Cabuz et al. |
| 6,589,792 B1 | 7/2003 | Malachowski |
| 6,592,822 B1 | 7/2003 | Chandler |
| 6,649,414 B1 | 11/2003 | Chandler et al. |
| 6,696,304 B1 | 2/2004 | Davies |
| 6,828,109 B2 | 12/2004 | Kaplan |
| 6,916,661 B2 | 7/2005 | Chandler et al. |
| 7,229,778 B2 * | 6/2007 | Hendrix et al. .............. 435/7.2 |
| 2002/0182609 A1 | 12/2002 | Arcot |
| 2003/0059764 A1 | 3/2003 | Ravkin et al. |
| 2003/0170739 A1 | 9/2003 | Iobst et al. |

FOREIGN PATENT DOCUMENTS

| | | |
|---|---|---|
| EP | 1 388 734 A1 | 2/2004 |
| EP | 1 394 274 A2 | 3/2004 |
| EP | 1 426 381 A1 | 6/2004 |
| WO | WO 96/02002 A1 | 1/1996 |
| WO | WO 97/14028 A2 | 4/1997 |

OTHER PUBLICATIONS

S. Baldwin, M. R. Odio, S.L. Haines, R. J. O'Connor, J. S. Englehart and A.T. Lane, "Skin Benefits from continuous topical administration of a zinc oxide/petrolatum formulation by a novel disposable diaper"; Journal of the European Academy of Dermatology and Venereology 2001 United Kingdom; vol. 15, Suppl. 1, pp. 5-11.

Mauricio R. Odio, Robert J. O'Connor, Frank Sarbaugh, and Sue Baldwin, "Continuous Topical Administration of a Petrolatum Formulation by a Novel Disposable Diaper: 1. Effect on Skin Surface Microtopography"; Dermatology (Basel), vol. 200, No. 3, 2000, pp. 232-237.

M. A. Farage-Elawar, N. A. Enane, S. Baldwin, F. C. Sarbaugh, C. Bergholz, and R. W. Berg, "A Clinical Method for Testing the Safety of Catamenial Pads"; Gynecologic and Obstetric Investigation, vol. 44, No. 4, Nov. 1997, pp. 260-264.

* cited by examiner

*Primary Examiner*—Herbert J. Lilling
(74) *Attorney, Agent, or Firm*—John G. Powell

(57) ABSTRACT

A method for determining the relative benefits of products which affect animal epithelial tissue is provided. Also provided is a method for evaluating quantitative changes on one or more affected surfaces of epithelial tissue of a subject caused by a test product.

12 Claims, 18 Drawing Sheets

| Location | Treatment group | Erythema mean value |
|---|---|---|
| Buttocks | Product | 0.69 |
|  | Control | 0.80 |
| Genital | Product | 0.48 |
|  | Control | 0.56 |
| Intertrigenous | Product | 0.81 |
|  | Control | 0.72 |
| Perianal | Product | 0.57 |
|  | Control | 0.70 |

Figure 1

| Location | Treatment group | BCA Total Protein mean value ug/mL |
|---|---|---|
| Buttocks | Product | 25.7 |
| | Control | 28.5 |
| Front Waist | Product | 13.0 |
| | Control | 16.1 |
| Genital | Product | 18.9 |
| | Control | 19.4 |
| Hip | Product | 20.1 |
| | Control | 25.2 |
| Intertrigenous | Product | 36.9 |
| | Control | 49.3 |
| Perianal | Product | 24.9 |
| | Control | 25.0 |

Figure 3

| Location | Treatment group | Keratins 1,10 mean value ng/mL |
|---|---|---|
| Buttocks | Product | 275.8 |
|  | Control | 438.1 |
| Front Waist | Product | 77.7 |
|  | Control | 117.3 |
| Genital | Product | 72.3 |
|  | Control | 90.6 |
| Hip | Product | 134.2 |
|  | Control | 184.2 |
| Intertrigenous | Product | 200.7 |
|  | Control | 219.1 |
| Perianal | Product | 142.4 |
|  | Control | 269.5 |

Figure 5

| Location | Treatment group | Keratin 6 mean value ng/mL |
|---|---|---|
| Buttocks | Product | 47.4 |
|  | Control | 74.6 |
| Front Waist | Product | 38.3 |
|  | Control | 37.6 |
| Genital | Product | 36.6 |
|  | Control | 81.9 |
| Hip | Product | 40.0 |
|  | Control | 55.9 |
| Intertrigenous | Product | 73.2 |
|  | Control | 100.0 |
| Perianal | Product | 36.2 |
|  | Control | 82.3 |

Figure 7

| Location | Treatment group | Involucrin mean value pg/mL |
|---|---|---|
| Buttocks | Product | 34.7 |
| | Control | 108.0 |
| Front Waist | Product | 20.5 |
| | Control | 27.1 |
| Genital | Product | 72.3 |
| | Control | 90.6 |
| Hip | Product | 71.5 |
| | Control | 43.2 |
| Intertrigenous | Product | 420.8 |
| | Control | 1152.0 |
| Perianal | Product | 27.0 |
| | Control | 152.7 |

Figure 9

| Location | Treatment group | ATP mean value μM |
|---|---|---|
| Buttocks | Product | 40.0 |
| | Control | 35.1 |
| Front Waist | Product | 35.7 |
| | Control | 31.4 |
| Genital | Product | 39.7 |
| | Control | 40.1 |
| Hip | Product | 32.0 |
| | Control | 34.6 |
| Intertrigenous | Product | 82.7 |
| | Control | 75.4 |
| Perianal | Product | 36.6 |
| | Control | 40.1 |

Figure 11

| Endpoint | Week | Product A Normalized to baseline Mean | Product B Normalized to baseline Mean |
|---|---|---|---|
| 1) BCA Protein | 1 | -3.855 | -3.015 |
| | 2 | 11.032 | 12.328 |
| | 4 | 10.202 | 5.094 |
| 2) Cortisol | 1 | -343.148 | -132.225 |
| | 2 | -40.096 | 11.367 |
| | 4 | 511.149 | -44.510 |
| 3) Involucrin | 1 | -2.835 | -21.237 |
| | 2 | 42.799 | -26.458 |
| | 4 | 34.806 | -43.442 |
| 4) Keratin 1,10 | 1 | -291.589 | -374.832 |
| | 2 | -167.520 | -294.201 |
| | 4 | -278.347 | -585.984 |
| 5) Keratin 6 | 1 | 23.748 | 17.493 |
| | 2 | -4.137 | -13.406 |
| | 4 | -6.081 | -23.477 |

Figure. 18

METHODS FOR DETERMINING THE RELATIVE BENEFITS AND/OR EVALUATING QUANTITATIVE CHANGES OF PRODUCTS ON EPITHELIAL TISSUE

CROSS REFERENCE TO RELATED APPLICATIONS

This application is a divisional of U.S. application Ser. No. 10/787,560, filed Feb. 26, 2004 now U.S. Pat. No. 7,229,778.

FIELD OF INVENTION

The present invention relates to methods for determining the relative benefits of products which affect animal epithelial tissue. Also provided are methods for evaluating quantitative changes on one or more affected surfaces of epithelial tissue of a subject caused by a test product. The present invention also provides for articles of commerce comprising informational indicia in association with the article of commerce comprising information on the relative benefits of one or more consumer products and one or more comparison products wherein the information is determined according to the methods of the present invention.

BACKGROUND OF THE INVENTION

In animals, especially vertebrates the major type of tissues are nerve, muscle, blood, lymphoid, epithelia and connective tissues. In epithelia tissue, cells are tightly bound together into sheets. Unlike other tissue, epithelia tissue extracellular matrix is almost totally absent and consists of a thin matt called the basal lamina, which under lies the cellular sheet. Epithelia tissue lines all the cavities and free surfaces of animals, and the specialized junctions between the cells enable the epithelia tissue to form barriers to the movement of water, solutes and cells from one body compartment to another. Examples of these cavities and free surfaces include skin, lungs, digestive tract, rectum and the like.

It is readily apparent that epithelia tissue is the first point of contact for a wide range of consumer products. Consumer products, such as those which are topically applied, inhaled, swallowed, ingested, inserted rectally, etc., all initially contact epithelia tissue and either intentionally or unintentionally have an effect on the epithelia tissue. Typically, the effect of the consumer product is difficult, if not impossible, and time consuming to precisely quantify, if such quantification is possible. Furthermore, any assertions made in connection with the benefits and/or comparison to other consumer products on contacting epithelia tissue would face strict legal and regulatory scrutiny not only by various government agencies but also other companies and various special interest groups.

Consequently, there remains the need for methods for evaluating the quantitative changes on epithelial tissue by consumer products and determining the relative benefits of products which affect epithelial tissue.

SUMMARY OF THE INVENTION

A first aspect of the present invention provides a method for evaluating quantitative changes on one or more affected surfaces of epithelial tissue of an animal subject caused by a test product, comprising the steps of:
  (a) harvesting one or more control surfaces of epithelial tissue from a subject to collect a first portion of mixed analytes as a test sample;
  (b) harvesting the affected surface of epithelial tissue from the subject of step (a) to collect a second portion of mixed analytes as a control sample;
  (c) identifying marker analytes in the test and control samples;
  (d) evaluating the effect of the product on the epithelial tissue by evaluating the quantitative changes on the affected areas of the epithelial tissue by comparing the marker analytes from the affected areas with the marker analytes from the control area.

A second aspect of the present invention provides a method for determining the relative benefits of products which affect animal epithelial tissue, comprising the steps of:
  (i) selecting one or more test products and one or more comparison products;
  (ii) applying the one or more test products and the one or more comparison products to one or more animal subjects to provide affected areas of epithelial tissue;
  (iii) determining the benefits of each of the one or more test products and each of the one or more comparison products by:
    (a) harvesting one or more control surface of epithelial tissue from a subject to collect a first portion of mixed analytes as a test sample;
    (b) harvesting the affected surface of epithelial tissue from of the subject of step (a) to collect a second portion of mixed analytes as a control;
    (c) identifying marker analytes in the test and control samples;
    (d) evaluating the effect of the product on the epithelial tissue by evaluating the quantitative changes on the affected areas of the epithelial tissue by comparing the marker analytes from the affected areas with the marker analytes from the control area;
  to provide comparative data between each of the one or more test products and each of the one or more comparison products; and
  (iv) comparing the data obtained in the step (c) to determining the relative benefits of the one or more test products and the one or more comparison products.

A third aspect of the present invention provides a method for obtaining cellular debris and secretions from epithelial tissue comprising the steps of:
  (a) obtaining a harvesting substrate comprising the cellular debris and secretions from epithelial tissue;
  (b) immersing the harvesting substrate in an effective amount of a harvesting solution; and
  (c) subjecting the immersed harvesting substrate to sonication.

It should be understood that every limit given throughout this specification will include every lower, or higher limit, as the case may be, as if such lower or higher limit was expressly written herein. Every range given throughout this specification will include every narrower range that falls within such broader range, as if such narrower ranges were all expressly written herein.

All percentages, ratios and proportions are by weight, and all temperatures are in degrees Celsius (° C.), unless otherwise specified. All measurements are in SI units unless otherwise specified.

BRIEF DESCRIPTION OF THE DRAWINGS

The above-mentioned and other features and objects of this invention and the manner of attaining them will become more apparent, and the invention itself will be better understood by reference to the following description of the invention taken in conjunction with the accompanying drawings, wherein:

FIG. 1 is a table illustrating Clinical erythema grades from four diapered skin locations according to example 1.

FIG. 3 is a table illustrating BCA total protein assay quantitation of protein removed from single D-squame® tapes from six diapered skin locations according to example 1.

FIG. 5 is a table illustrating Bead assay quantitation of keratins 1&10 removed from single D-squame® tapes from six diapered skin locations according to example 1.

FIG. 7 is a table illustrating Bead assay quantitation of keratins 6 removed from single D-squame® tapes from six diapered skin locations according to example 1.

FIG. 9 is a table illustrating Bead assay quantitation of involucrin removed from single D-squame® tapes from six diapered skin locations according to example 1.

FIG. 11 is a table illustrating Luciferase assay quantitation of ATP removed from single D-squame® tapes from six diapered skin locations according to example 1.

FIG. 18 is a table illustrating the data as illustrated in the bar graphs of FIGS. 13 to 17.

DETAILED DESCRIPTION OF THE INVENTION

Definitions

Figure 2:
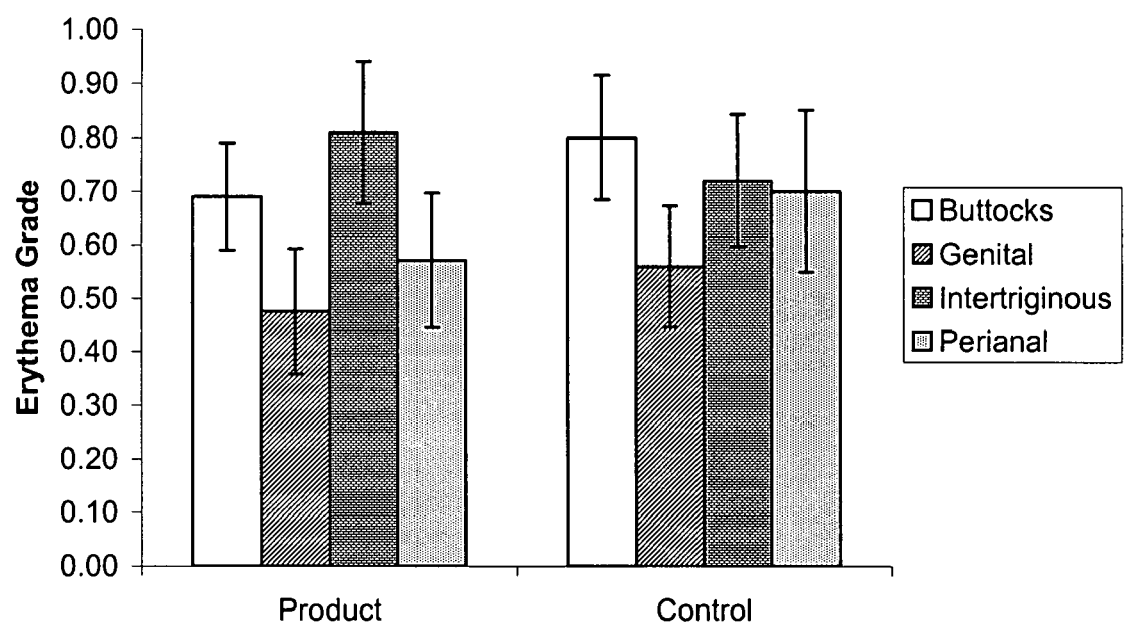
FIG. 2 is a bar graph of the data from the table of FIG. 1.
Figure 4:
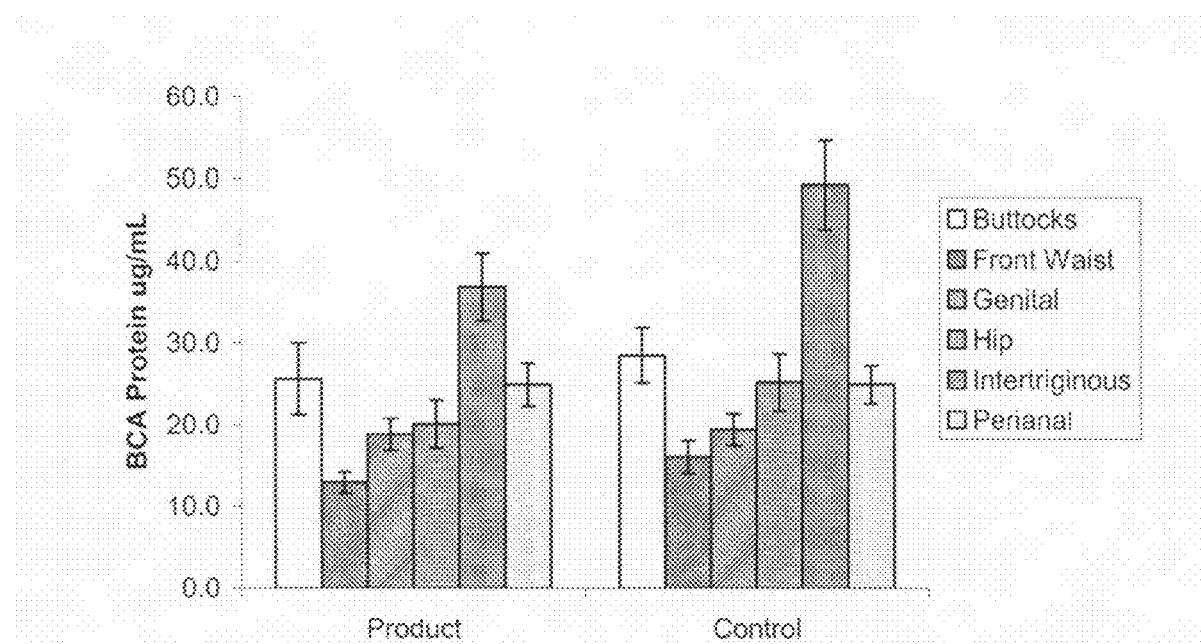
FIG. 4 is a bar graph of the data from the table of FIG. 3.
Figure 6:
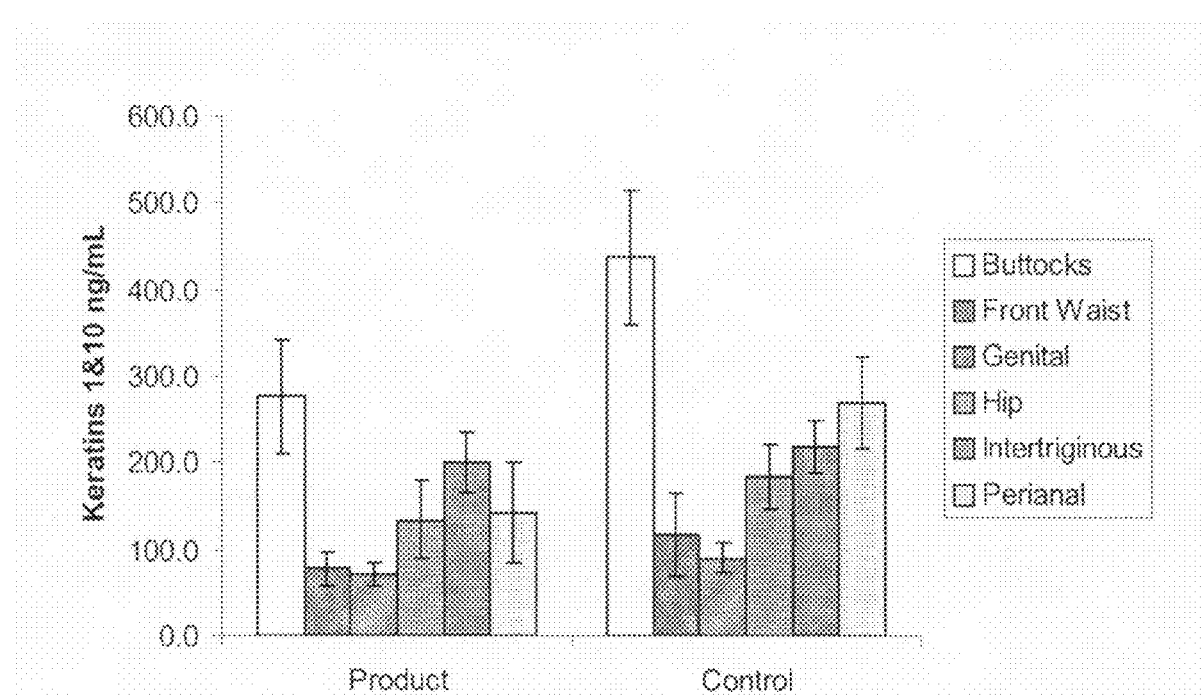
FIG. 6 is a bar graph of the data from the table of FIG. 5.
Figure 8:
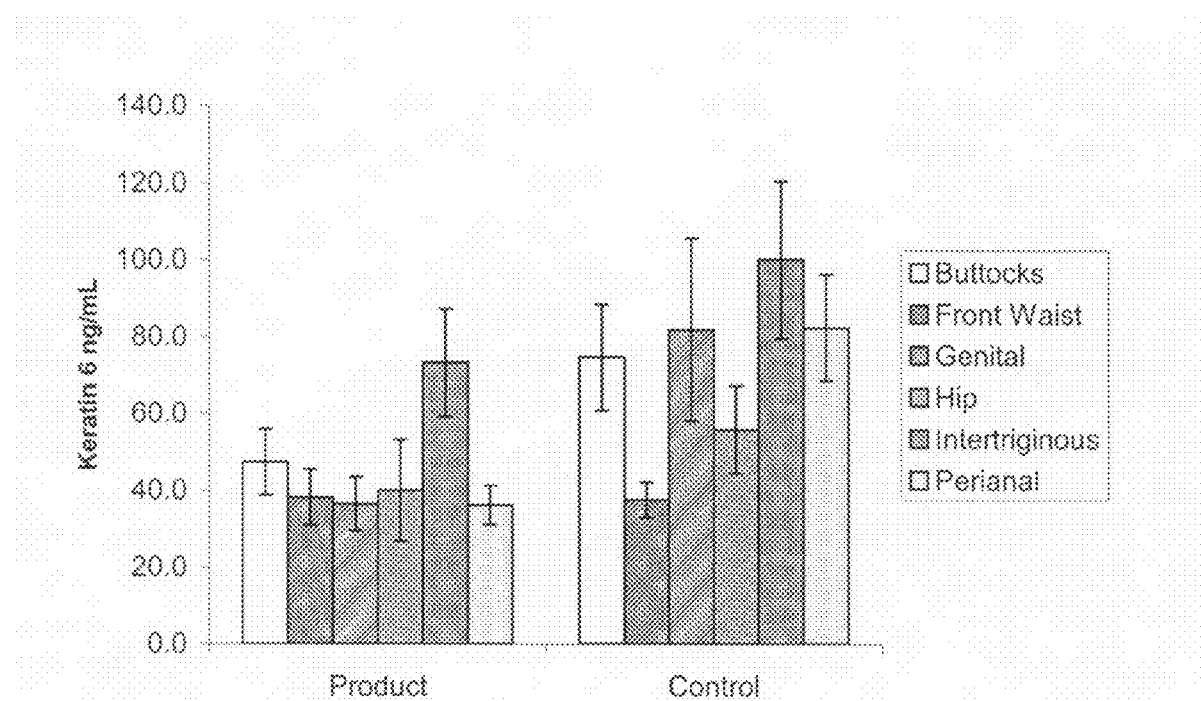
FIG. 8 is a bar graph of the data from the table of FIG. 7.
Figure 10:
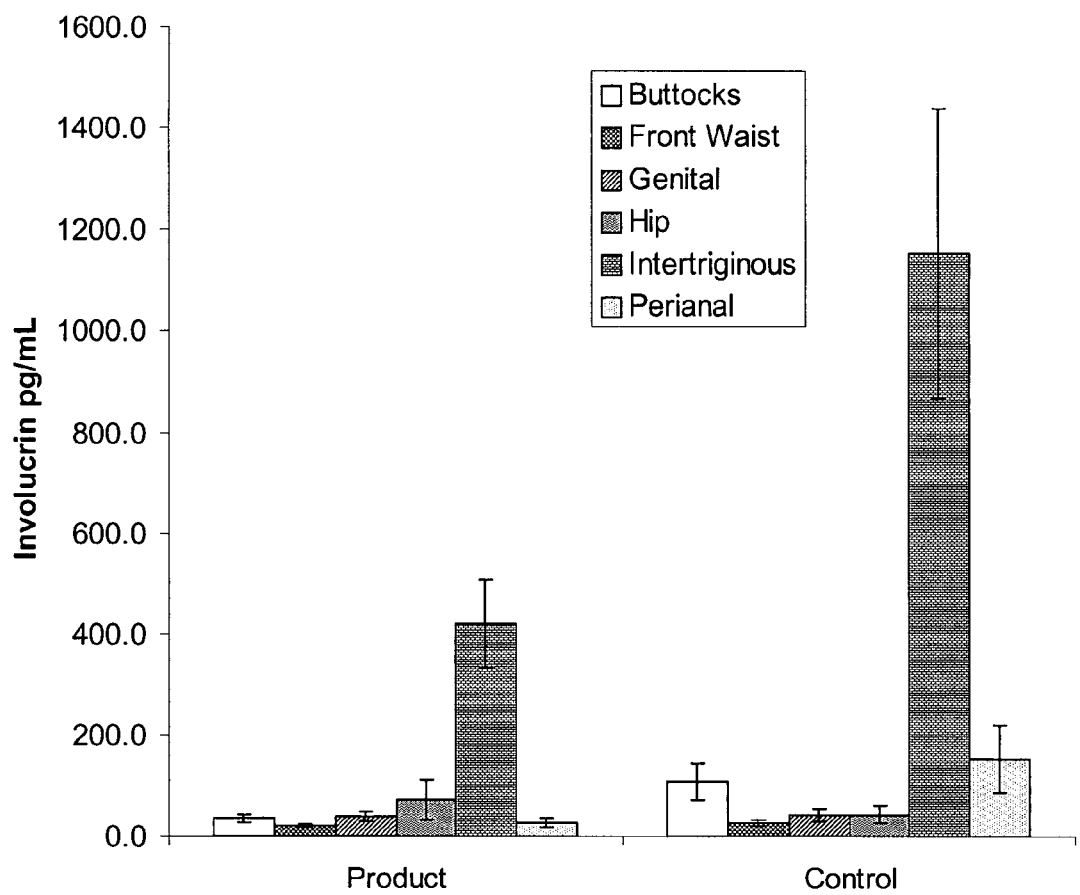
FIG. 10 is a bar graph of the data from the table of FIG. 9.
Figure 12:
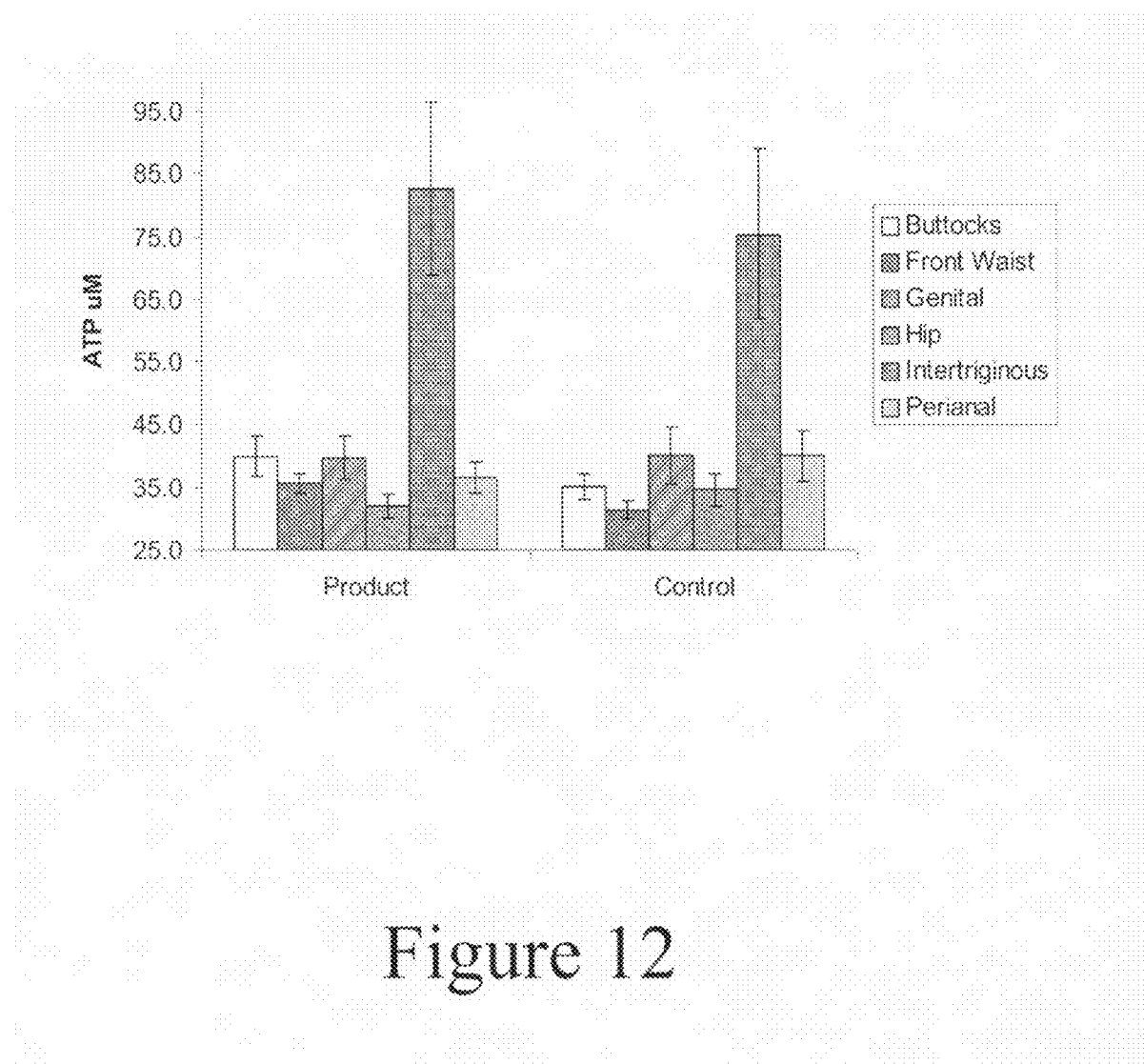
FIG. 12 is a bar graph of the data from the table of FIG. 11.
Figure 13:
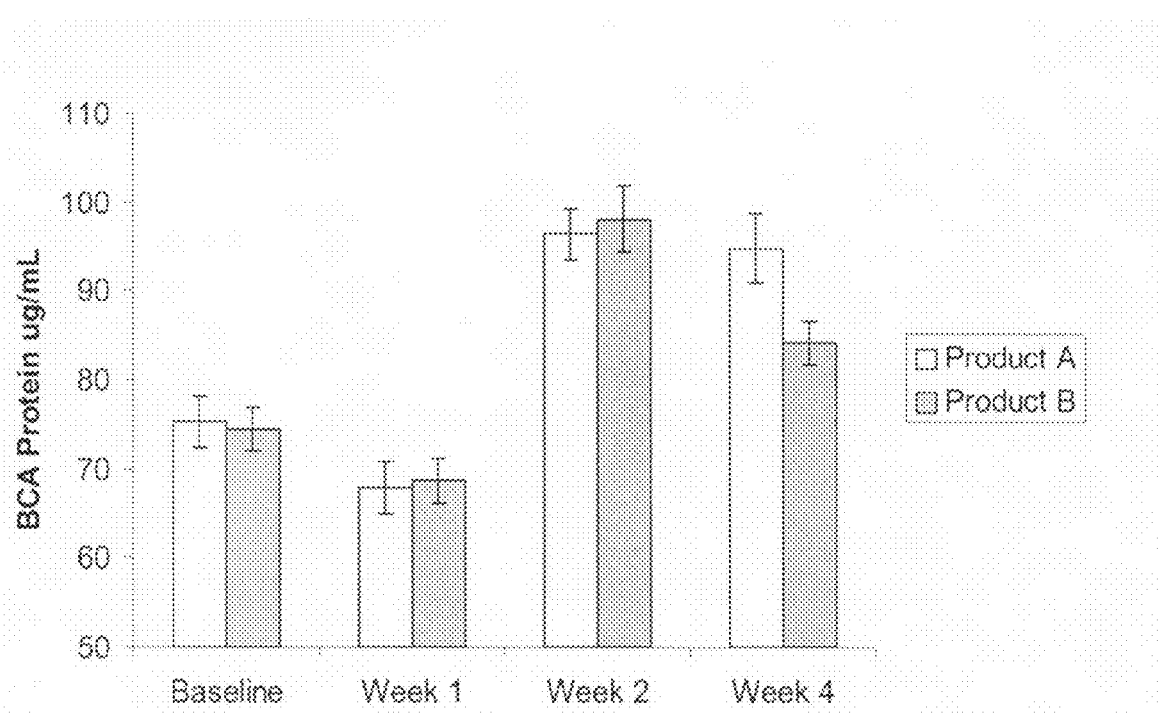
FIG. 13 is a bar graph illustrating BCA Total Protein assay mean of tapes 2, 4, and 6 for each product and each time according to example 5.
Figure 14:
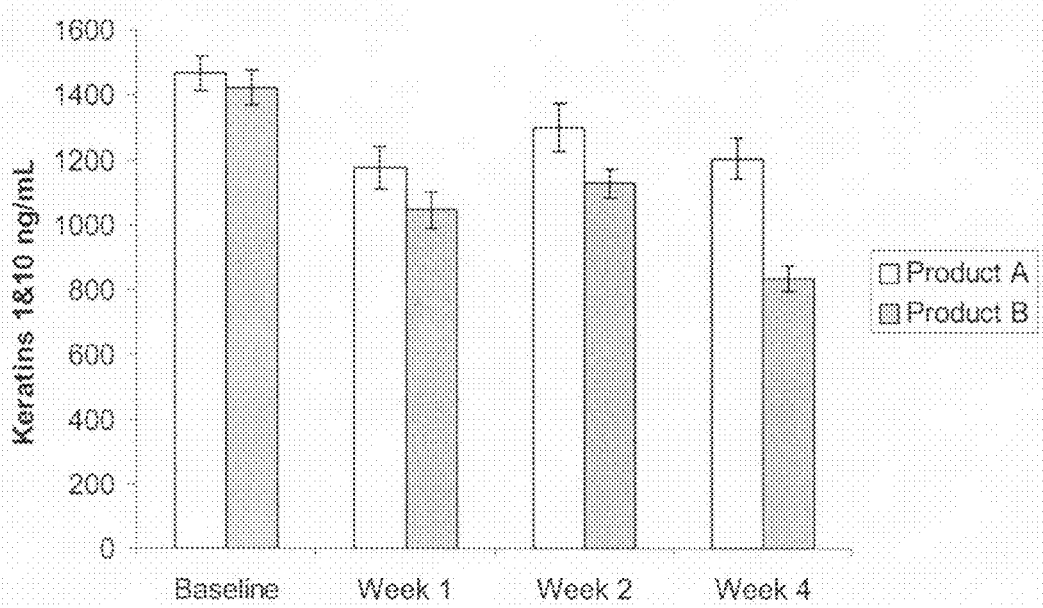
FIG. 14 is a bar graph illustrating Bead assay for keratins 1&10 mean of tapes 2, 4, and 6 for each product and each time according to example 5.
Figure 15:
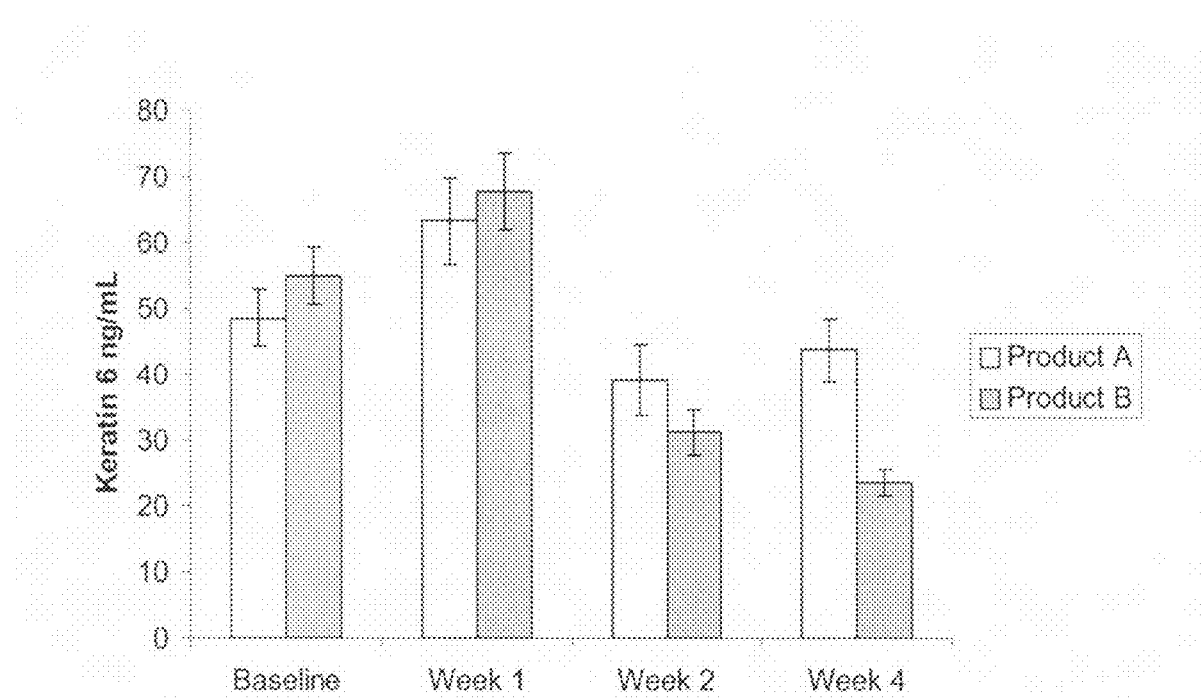
FIG. 15 is a bar graph illustrating Bead assay for Keratin 6 mean of tapes 2, 4, and 6 for each product and each time according to example 5.

As used herein, the term "comprising" means that the various components, ingredients, or steps, can be conjointly employed in practicing the present invention. Accordingly, the term "comprising" is open-ended and encompasses the more restrictive terms "consisting essentially of" and "consisting of." Other terms may be defined as they are discussed in greater detail herein.

As used herein, the term "animals" includes all multi cellular animals which have epithelia tissue, and includes both vertebrates and invertebrates. Typically, the term "animals" includes, both wild and domestic varieties of terrestrial and aquatic animals, such as mammals, reptiles, amphibians, birds, fish and the like. Examples of animals meeting this definition include, but are not limited to, llamas, parrots, albatross, rabbits, moose, snipe, humans, cows, ferrets, pigs, chickens, sheep, crocodiles, shellfish, alligators, sharks, salmon, emus, ducks, turkeys, geese, horses, octopus, squid, dogs, cats, mice, hamsters, rats, lions, buzzards, rhinos, dolphins, pandas, lizards, wombats, platypus, kangaroos, monkeys, chimpanzees, lemurs, gibbons, gorillas, baboons and marmosets. Also included in this definition are naturally occurring animals and the so called transgenic animals or man made or modified animals, such as but not limited to, the "Harvard mouse", glow-in-the dark zebra fish and the like.

Epithelial Tissue

The term "epithelia" as used herein means a tissue comprising a sheet of cells, one or several layers thick, organized above a basal lamina, and often specialized for mechanical protection or active transport. The epithelia tissue comprises several distinct layers of tissue. The deepest layer is the stratum basalis layer, which consists of columnar cells. The overlying layer is the stratum spinosum, which is composed of polyhedral cells. Cells pushed up from the stratum spinosum are flattened and synthesize keratohyalin granules to form the stratum granulosum layer. As these cells move outward, they lose their nuclei, and the keratohyalin granules fuse and mingle with tonofibrils, which in the palm or base of foot forms a clear layer called the stratum lucidum. The cells of the stratum lucidum are closely packed. As the cells move up from the stratum lucidum, they become compressed into many layers of opaque squamae. These cells are all flattened remnants of cells that have become completely filled with keratin and have lost all other internal structure, including nuclei. These squamae constitute the outer layer of the epithelia tissue, the stratum corneum. At the bottom of the stratum corneum, the cells are closely compacted and adhere to each other strongly, but higher in the stratum they become loosely packed, and eventually flake away at the surface.

Some non-limiting examples of specific epithelia tissue include, skin, eyes, sinus cavities, outer ear, throat, stomach, urethra, bladder, lungs, digestive tract or bowels, anus, rectum and the like.

The term "affected surface" as used herein means a region of epithelia tissue which has been contacted with and/or by a product, such as a consumer product and/or a test product, and the contact of the product on the epithelia tissue has resulted in some change, such as but not limited to, physiological, biochemical, visible, and/or tactile changes, in and/or on the epithelia tissue. Illustrative and non-limiting examples of such affected surfaces include, discoloration of the skin, diaper rash, dermatitis, inflammation, eczema, flaking of the epithelia tissue such as dandruff, edema, hyperexfoliation and the like. The affected surface is not limited to regions of epithelia tissue which have had deleterious effects caused by product, also included are regions of epithelia tissue which have had positive effects caused by product, such as but not limited to, reduction in erythema, reduction in transepidermal water loss (TEWL) reduction in discoloration of the skin, reduction in diaper rash, reduction in dermatitis, reduction in inflammation, reduction in sensing irritation in eczema, reduction in dandruff, reduction in edema and the like. The location of the affected surface will depend upon the product used or the location of some physiological, biochemical, visible, and/or tactile change in and/or on the epithelia tissue. For example, in the case of a diaper or a baby lotion the affected surface would typically be epithelia tissue, in this case skin, from a child's buttocks, groin, genitalia, perianal, inner leg fold and combinations thereof.

The term "control surfaces" as used herein means a region of epithelia tissue which has not been contacted with and/or by the product, such as a consumer product and/or a test product, which has contacted the affected surface. Typically, control surface is will be of similar epithelia tissue which has not contacted the product. For example, returning to the in the case of a diaper or a baby lotion the affected surface would typically be epithelia tissue, in this case skin, from a child's buttocks, groin, genitalia, perianal, inner leg fold and combinations thereof, whereas the control surface would be apportion of the skin which has contacted the product, such as but not limited to sternum, top of the foot and combinations thereof.

Alternatively, the control surface may be the same epithelial tissue as the affected surface. In this case the control surface is harvested some time prior, such as from 1 second to 5 or 6 weeks or possibly even longer to the application of the test product and/or comparison product to the epithelial tissue, which is then harvested to collect the test sample.

Method for Evaluating Quantitative Changes

The first aspect of the present invention is a method for evaluating quantitative changes on one or more affected surfaces of epithelial tissue of a subject caused by a test product. This evaluation method allows for a relatively simple, efficient and quick determination of a test products effect on epithelial tissue. The method is a highly flexible tool to enable the user to determine what effects, both positive and negative, a test product has on epithelial tissue.

Harvesting

The methods of the present harvest epithelial tissue to collect a portion of mixed analytes. Any method suitable for harvesting portion of epithelial tissue to collect a portion of mixed analytes may be used provided the method obtains cellular debris and secretions from the epithelial tissue. Non-limiting examples of suitable harvesting techniques includes, application of tape, rinsing by lavage method, biopsy, swabbing, scraping, blotting and combinations thereof. However, whichever harvesting technique is used, it must be one where the only mixed analytes obtained are those present on the outer surface of, and/or in the epithelial tissue and not include any of the underlying non-epithelial tissue, e.g., if the harvesting method was biopsy of the skin, then the biopsy must only be of skin epithelial tissue and not include any of the underlying non-epithelial tissue, such as muscle.

Typically the harvesting method employed will depend upon may factors, such as but not limited to, the location of the epithelial tissue (e.g., skin, nose, rectum, lungs, etc.), the size of the epithelial tissue (i.e., how thick is the epithelial tissue), the area of the epithelial tissue, the animal from which the epithelial tissue is being harvested (e.g., a babies bottom, compared to crocodiles mouth), how much epithelial tissue is required, location of the animal from which the epithelial tissue is being harvested, and the like.

One suitable method of harvesting epithelial tissue is by application of tape, such as but not limited to any type of medical tape. This harvesting technique is relatively simple to use and includes application of a tape to the epithelial tissue, typically for tape this is the skin, which is then removed therefrom. The mixed analytes obtained from the epithelial tissue and present on the tape are then removed from the tape in any fashion that maintains the structural integrity of the mixed analytes. By "maintain the structural integrity" it is meant that any mixed analytes removed from the epithelial tissue are removed from the tape in any fashion that preserves the mixed analytes in approximately the same configuration and/or structure they had when they were present in and/or on the epithelial tissue.

The size or amount of tape used which contacts the epithelial tissue will also vary upon many factors, including but not limited to the location of the epithelial tissue, the size of the epithelial tissue, the area of the epithelial tissue, the animal from which the epithelial tissue is being harvested, how much epithelial tissue is required, location of the animal from which the epithelial tissue is being harvested, and the like. In any event the size of the tape used should be of similar, if not approximately identical size for the harvesting all the portions of mixed analytes. In one optional embodiment of the present invention the size of the tape used to harvest epithelial tissue, i.e., how much of the tape actually contacts the epithelial tissue for the harvest, is from about 2.5 mm$^2$ to about 50 mm$^2$.

In one optional embodiment of the present invention, the mixed analytes present on the tape are removed therefrom prior to identification of the mixed analytes present. In one preferred embodiment of this optional embodiment, the mixed analytes present on the tape are removed by application, of a liquid such as medical saline (typically an aqueous solution comprising 0.9% by weight of aqueous solution of saline available from any suitable supplier of medical saline, such as Besse Medical Supply, of West Chester, Ohio USA) or a harvesting solution, which is described in more detail herein. The liquid may contact the tape in any fashion suitable to remove the mixed analytes present, for example by immersion, rinsing, misting and the like or combinations thereof. It is also possible to apply energy, typically via sonication (i.e., application of sonic and/or ultrasonic energy, preferably only sonic energy) concurrent with and/or subsequent to contacting the tape with the liquid. One preferred embodiment of the present invention the mixed analytes present on the tape are removed therefrom by immersion in a harvesting solution which is then subjected to sonication.

In one optional embodiment of the present invention from about 100 μL to about 2.0 mL of harvesting solution is used per 39.774 mm$^2$ of tape. Alternatively, from about 0.0025 mL to about 0.5 mL of harvesting solution is used per mm$^2$ of tape, more preferably 1 mL of harvesting solution for every 39.774 mm$^2$ of tape.

In one optional embodiment of the present invention the mixed analytes are removed from the tape containing them, by placing the tape in an appropriate size closable container, i.e., a container that can hold the entire sample of tape, solution, and close. Suitable containers include, but are not limited to, silanized borosilicate vials, such as those available from National Scientific, Duluth, Ga., USA. Once the tape and solution are present in the closable container they are subjected to sonication. The sonication acts to assist the solution in removing the mixed analytes from the tape by shaking them loose. Typically, the container is subjected to the sonication while at a temperature below room temperature, typically while present in an ice water bath, i.e., from about 0° C. to about 10° C. While not wishing to be limited by theory, it is believed that this lower temperature helps maintain the structural integrity of the mixed analytes while they are being removed from the tape. The duration and intensity of the sonication will depend upon may factors, such as but not limited to, the type of tape used, the size of the tape used, the liquid used, the nature of the mixed analytes (e.g., is there a significant percentage of fat molecule present or is there a significant protein content, how stable are the mixed analytes to sonication, etc.), the epithelial tissue and the like. The container and the contents therein (i.e., tape and liquid) are subjected to sonication for a time which will remove the maximum amount of mixed analytes while maintain the structural integrity of the mixed analytes, preferably the container and the contents therein are subjected to sonication for a time from about 5 minutes to about 1 hour, more preferably from about 15 to about 30 minutes. Similarly, the frequency and intensity of the sonication are selected to remove the maximum amount of mixed analytes while maintain the structural integrity of the mixed analytes, preferably the sonicator is used at a frequency of from about 18 to about 50 kHz and an intensity of from about 10 to about 100 watts. Examples of suitable sonicators include, but are not limited to, Bransonic Models 5510 Ultrasonic Cleaner and B300 Ultrasonic Cleaner both of which are available from Branson, Danbury, Conn., USA.

Exemplary tapes include, but are not limited to: D-squame tape®, and SEBUTAPE®, both of which are available from CuDerm Corporation, Dallas, Tex., USA; and Transpore® tape which is available from the 3M company, of Minnesota USA.

Another suitable harvesting method is rinsing by lavage method, which is especially useful for some epithelial tissue, such as but not limited to, ear, nasal passages, mouth, rectum, and the like. Rinsing by lavage method involves contacting the epithelial tissue with a liquid, such as but not limited to, water, medical saline, the harvesting solution as described herein and the like, and collecting the run off liquid containing the mixed analytes, in a container.

In the rinsing by lavage method the liquid is applied to the epithelial tissue with sufficient force to pick up any cellular debris as well as any secretions, preferably from about $1 \times 10^{-5}$ to about 9.81 Newtons. This force may be applied during the delivery of the liquid to the epithelial tissue and/or during the recovery of the liquid from the epithelial tissue, for example squirting a solution up an animals nose, asking the subject to blow their nose and recovering the material ejected during the blow.

Other suitable harvesting methods are well known and include, but are not limited to, biopsy, such as, shave biopsy, punch biopsy and the like; scraping i.e., some type of physical ablation of the epithelial tissue; blotting, such as via a nitrocellulose blotting membrane which is then wetted with a liquid such as but not limited to, medical saline or the harvesting solution, which is then treated to remove the mixed analytes thereon by an suitable means, with the use of the harvesting solution and sonication, as detailed herein being preferred; swabbing, typically performed with cotton swabs, nitrocellulose blotting membrane, gauze and the like, which are then treated to remove the mixed analytes thereon by an suitable means, such as but not limited to, the use of a liquid, such as the harvesting solution detailed herein and optionally sonication as detailed herein; and by collection of mixed analytes from an object which has been and/or is in contact with the epithelial tissue, such as but not limited to, consumer products, such as but not limited to, used wet wipes (baby/facial), used tissues, used diapers, articles of clothing or portions thereof and the like which have been worn and not yet cleaned, e.g., socks, underwear, shirt collars, bed linen, towels and the like; used personal care objects, such as but not limited to, tooth brushes, hair brush, brush for a pet, etc.; and the like.

Additional optional process steps, such as but not limited to, stabilizing the harvested epithelial tissue, e.g., using reagents to adjust pH, lyse cells, or inhibit nascent enzymatic activity.

It is also within the scope of the present invention to use combinations of harvesting techniques. Furthermore, while it is not essential it is nevertheless preferred that which ever harvesting technique is used to obtain the first portion of mixed analytes for the test sample it is preferred that the same harvesting technique is used to obtain the second portion of mixed analytes for the control.

Harvesting Solution—In one optional embodiment of the present invention the mixed analytes on a harvesting substrate, such as but not limited to tape, nitrocellulose blotting membrane, cotton swabs, gauze, articles of clothing and the like, may be removed by the application of a harvesting solution. Alternatively, the harvesting methods, such as but not limited to rinsing by lavage method (as described herein) and the like, the harvesting solution is directly applied to the epithelial tissue to harvest the mixed analytes.

The harvesting solution may comprise a variety of ingredients. Suitable ingredients include but are not limited to: solvents, such as water (which may be tap, rain, mineral, distilled, filtered, and/or deionised), ethanol, other alcohols, polyethylene glycols and the like, and combinations thereof; surfactants, such as anionic surfactants, nonionic surfactant and combinations thereof; salts, such as NaCl, KCl, NaF, KF, tetramethylammonium chloride (TMAC), and the like, and combinations thereof; base, such as alkali metal hydroxides, ammonium hydroxides and combinations thereof; acid, such as but not limited to sulfuric acids; penetration enhancers, such as but not limited to, glycols, especially propylene glycol, DMSO and combinations thereof; buffers, such as phosphate buffers, citrate buffers, and the like; and combinations thereof; and mixtures thereof.

The ingredients, when present in the harvesting solution, are each typically employed in compositions at levels of from about 0.0001% to about 99.9%, preferably from about 0.001% to about 99%, and more preferably from about 0.01% to about 97%, by weight of the harvesting solution.

In one optional embodiment of the present invention the harvesting solution comprises:
  (i) from about 50% to about 99.9%, more preferably from about 75% to about 99.9%, by weight of the harvesting solution of water, more preferably deionized and/or distilled water;
  (ii) from about 0.00001% to about 5%, more preferably from about 0.0001% to about 2.5% by weight of the harvesting solution of salts or phosphate containing salts, more preferably sodium phosphate, potassium phosphate, NaCl, KCl, NaF, KF, TMAC, sodium citrate, and combinations thereof;
  (iii) from about 0.0001% to about 5%, more preferably from about 0.001% to about 2.5% by weight of the harvesting solution of a surfactant, more preferably an anionic surfactant, a nonionic surfactant and mixtures thereof, even more preferably sodium dodecyl sulfate; and
  (iv) from about 0.001% to about 10% more preferably from about 0.001% to about 5.0% by weight of the harvesting solution of a glycol, more preferably propylene glycol.

The pH of the harvesting solution may be any suitable and will vary depending upon many factors, such as but not limited to, the harvesting method used, the mixed analytes present, ingredients present in the harvesting solution, the epithelial tissue harvested, etc. Typically, pHs in the range of from about 1 to about 11 is suitable. However, a pH in the range of from about 6.5 to about 8.0, even more preferably from about 7.0 to about 8.0, is more preferred especially when the epithelial tissue is skin. The pH is measured on the neat harvesting solution at a temperature of about 25° C. and about one atmosphere of pressure.

Mixed Analytes and Marker Analytes

Mixed Analytes—The mixed analytes harvested from the epithelial tissue may include a wide range of different materials, which may range from, for example, compounds, and/or microflora found naturally on and/or in epithelial tissue to portions or entire cells from the epithelial tissue. The mixed analytes may also include material not typically found on and/or in epithelial tissue, such as, but not limited to, consumer products, viruses, or similar normative microflora. The mixed analytes harvested from the epithelial tissue will depend upon many factors, including but not limited to the epithelial tissue harvested. Non-limiting examples of such analytes include: epithelial tissue and parts thereof; consumer products or parts thereof, such as those consumer products disclosed herein; animal fluids, excretions and the like or components thereof, such as but not limited to urine, sweat, blood, puss, tears, menses, seminal fluid, salts, glucose, urea, bile, mucus, sputum, saliva, snot, nasal discharges, ear wax, deposition on epithelial tissue from gaseous emissions (such as, but not limited to, exhaled breath, burps, sneezes, flatulence and the like) and the like; microflora and their products and the like which are resident in and/or on the harvested epithelial tissue, such as but not limited to, C. albicans; E. coli; S. aureus, dust mite dander, allergens; insect or other animal by-products due to biting or stinging, and the like.

Marker Analytes—Marker analytes are the analytes present in the test and control samples that are identified by the antibody probes in order to evaluate the effect of a product on the epithelial tissue. The marker analytes are a subset of the mixed analytes present in the test and control samples.

The number of marker analytes will vary depending upon the benefits of a product and/or the quantitative changes to epithelial tissue that is being evaluated. Typically there will be one or more, preferably two or more marker analytes for any particular process of the present invention.

The choice of marker analyte will depend upon may factors, including but not limited to, the quantitative changes being evaluated, the location of the epithelial tissue, the epithelial tissue, test product used, comparison product(s), benefits being compared, and the like.

Some non-limiting examples of possible marker analytes include: Alpha-actinin; alpha-catenin; actin; actin binding proteins; catenins; cytokeratins type I; cytokeratins type II; skin chymotrypsin-like enzymes; cytokeratins type I; cytokeratins type II; Desmogelin 1 and other desmogleins; fibronectin and fibronectin associating proteins; hyaluronic acid; involucrin; intergrins; intercellular adhesion molecules; human serum albumin; E-cadherin and classical family members such as but not limited to desmocollin; profillagrin and its break down products including, but not limited to, natural moisturization factor (NMF) and the amino acids from it; cellular retinoid binding proteins; ceramides; Cholesterol and biological modifications of cholesterol including, but not limited to, hormones such as cortisol and testosterone; proteoglycans including heparan and chondroitin-6 sulfate; keratin associated proteins; loricrin; trichohyalin; Collagen, such as but not limited to, collagens of the basement membrane such as, but not limited to, collagens I, III and IV, and collagen-associated proteins such as, but not limited to, nidogen and laminin; collagenases; cornifin; calcium binding proteins, such as but not limited to S100; desmocollins; desmogleins; desmoplakin; keratohyalin; sphingolipids; total disulfide bond content for the concentration within the sample of cysteine cross-links; inositol containing compounds; melanization signal pathways including, but not limited to, alpha-MSH, microtubules composed of tubulin and associated proteins including, but not limited to, microtubule associated protein one (MAP1) and the like; intermediate filaments such as, but not limited to, the keratins, lamins, and vimentin and associating proteins such as but not limited to, plakoglobin; kalinin; plectin; keratohyalin granules and the proteins contained within them; laminin; lipids; lipoproteins; nidogen; pancomulins; cornifin; keratolinin; profilin; cross-linking cell envelope proteins; envelope pre-cursor proteins; retinoic acid binding proteins; SPARC; small proline rich proteins (SPRR) including, but not limited to, SPRR1, 3, and 4; spectrin and spectrin-like proteins; talin; keratinocyte transglutaminase-1 and other soluble transglutaminases; syndecan; tenascin; tensin; trichohyalin; triglycerides; tubulin; tyrosinases and their enzymatic products; vimentin; vinculin; cellular division markers such as, but not limited to, cyclins and cyclin dependent kinases; diffipoptosis (differentiation) markers such as but not limited to, caspase 14; and apoptosis markers and indicators such as, but not limited to, bax and bcl-2; alpha-melanocyte stimulatory hormone; arachidonic acid and its metabolites such as, but not limited to, thromboxane, prostaglandins, and leucotreines; basic fibroblastic growth factor; vitamins; minerals (esp. Zinc, Calcium, Magnesium, etc.); cytokines/chemokines (expressed by epithelial cells); epithelial growth factors; retinoic acid; sebocyte products; and eccrine gland products; C. albicans; E. coli; S. aureus; other microflora resident and their products in and/or on epithelia; dust mite dander; allergens; insect by-products due to biting or stinging and the like.

Identification of Marker Analytes

The various portions containing the mixed analytes are analyzed to identify any marker analytes present. As noted herein, the marker analytes are preferably identified via antibody probes or highly specific chemical interactions. Non-limiting examples of suitable non-antibody identification include but are not limited to, colorimetric and fluorometric probes which can be added to a portion of the sample to examine enzyme content, total protein, DNA content and the like. Many of these over the counter kits are produced by Molecular Probes, Inc. 29851 Willow Creek Road, Eugene, Oreg. 97402. Additional non-antibody identification techniques may include, but are not limited to, specific reactions, such as any high affinity binding between ligands/receptors, enzymes/inhibitors, enzymes/activators/enzyme/substrate and the like. An illustrative, non-limiting example of one of these non-antibody identification includes total protein content. Non-limiting examples of analysis of total protein content may be done, for example, by utilizing reagents, such as but not limited to bicinchoninic acid, modified Lowry and Bradford Coomassie blue techniques. Another illustrative non-antibody identification includes examination of DNA such as but not limited to, of evaluation of total DNA content by methods, such as but not limited to, binding of the DNA to propidium iodide, or qualitative evaluation of the DNA through the us of molecular probes, such as but not limited to PicoGreen®, available from Molecular Probes Eugene Oreg., Fluorogenic substrates for glycosidases, peptidases, dealkylases, peroxidases, and esterases also available from Molecular Probes Eugene Oreg.

Antibodies or combinations of antibodies are employed to capture specific marker analytes obtained during the harvesting step. Antibodies are molecules that bind specifically to particular molecules that they are produced against. Antibodies can be monoclonal whereby they bind one specific region of a particular molecule, or can be polyclonal in which they bind many locations of a particular molecule. Other proteins can be employed that bind specific molecules, these are called lectins and within the context of assays can perform the same functions as antibodies. In order to capture and quantitate the amount of a particular molecule in a sample, typically antibodies are anchored to a substrate, such as a plastic plate, to permit the removal of the molecule from solution, this permitted the isolation of the molecule of interest. Upon isolation and rinsing a second antibody can bind the particular molecule with a color tagging system. The increases in color upon a substrate would indicate the isolation of more of the molecule of interest. If a known quantity of the molecule of interest was diluted in a series, this dilution could be used as a method to compare to the unknown concentration of a particular molecule from a sample. Known quantities of molecules can be considered standards, and a dilution of these standards can provide standard curves with which to reference. If only one antibody is available, or the molecule of interest is small, thereby making it difficult to have two separate binding locations for antibodies, one can produce what is called a competition assay. In this form of molecule identification a portion of the standard is chemically modified or "tagged", such as covalent attachment to trinitrophenol (TNP) or an enzyme such as horseradish peroxidase (HRP). This chemically modified standard is now a competitor. It is utilized by adding this competitor to the substrate with a specific antibody, then the addition of sample or standard. The competitor competes for binding to the substrate with the sample or standard added. After rinsing a second antibody with the ability to provide color, raised to the tag TNP or HRP binds to the competitor only. When examining the standard curves produced by these competition assays the highest quantities of a particular molecule have the lowest color, and the lowest quantity of a particular molecule have the highest color. A modification to the competition assay would be to bind a known quantity of the particular molecule to the substrate. Then add a sample and an antibody specific to the particular molecule. After rinsing, add a color indicating system against the antibody. Again, when examining the standard curves from the competition systems the highest quantities of a particular molecule have the lowest color, and the lowest quantity of a particular molecule have the highest color. Each of these systems of detection outlined above is performed within the context of immunosorbent assays known which are typically produced to use within tubes or wells of a plastic plate. However recent technologies have micronized the plastic assay plate to permit the anchoring substrate to be micronized, and allow the assay to take place in a solution format.

One method which is capable of concurrently identifying several marker analytes is flow cytometry. Flow cytometry is an optical technique that analyzes particular particles in a fluid mixture based on the particles' optical characteristics using an instrument known as a flow cytometer. Background information on flow cytometry may be found in Shapiro, "Practical Flow Cytometry," Third Ed. (Alan R. Liss, Inc. 1995); and Melamed et al., "Flow Cytometry and Sorting," Second Ed. (Wiley-Liss 1990).

Flow cytometers hydrodynamically focus a fluid suspension of particles into a thin stream so that the particles flow down the stream in substantially single file and pass through an examination zone. A focused light beam, such as a laser beam illuminates the particles as they flow through the examination zone. Optical detectors within the flow cytometer measure certain characteristics of the light as it interacts with the particles. Commonly used flow cytometers such as the Becton-Dickinson Immunocytometry Systems "FACSCAN" can measure forward light scatter (generally correlated with the refractive index and size of the particle being illuminated), side light scatter (generally correlated with the particle's size), and particle fluorescence at one or more wavelengths. (Fluorescence is typically imparted by incorporating, or attaching a fluorochrome within the particle.) Alternatively or in addition to optical characterization, the particles may be distinguished by their magnetic properties. Flow cytometers and various techniques for their use are described in, generally, in "Practical Flow Cytometry" by Howard M. Shapiro (Alan R. Liss, Inc., 1995) and "Flow Cytometry and Sorting, Second Edition" edited by Melamed et al. (Wiley-Liss, 1990).

A similar system to flow cytometry is available from the Luminex Corporation, Austin, Tex., USA and these allow for rapid detection of multiple customized marker analytes in real-time on small sample volumes, typically 5 to 50 µL per sample. This system is detailed within WO 97/14028 and U.S. Pat. No.: 6,592,822 issued to Chandler et al.; U.S. Pat. No. 5,981,180 issued to Chandler; U.S. Pat. No. 6,528,165 issued to Chandler et al.; U.S. Pat. No. 6,524,793 issued to Chandler; U.S. Pat. No. 6,514,295 issued to Chandler et al.; U.S. Pat. No. 6,449,562 issued to Chandler et al.; U.S. Pat. No. 6,411,904 issued to Chandler; U.S. Pat. No. 6,366,354 issued to Chandler; U.S. Pat. No. 6,268,222 issued to Chandler et al.; U.S. Pat. No. 6,139,800 issued to Chandler; U.S. Pat. No. 6,046,807 issued to Chandler.

In one embodiment of the present invention one type of "particle" analyzed by a flow cytometer or the like may be man-made microspheres or beads. Microspheres or beads for use in flow cytometry or the like are generally known in the art and may be obtained from manufacturers such as Spherotech, Beckman Coulter, and Molecular Probes. One preferred type of microspheres or beads is the Luminex Bio-Plex assays of the Multiplex Bead Technology of Bio-Rad Laboratories of Hercules, Calif. USA. The Multiplex Bead Technology using Bio-Plex assays allows for the rapid analysis, i.e., almost simultaneous if not simultaneous, analysis of a plurality of marker analytes. One Bio-Plex assay which is suitable for use in one optional embodiment of the present invention is the Bio-Plex protein array system which is capable of identifying up to 100 marker analytes. Additional information on, Multiplex Bead Technology, Bio-Plex assays and Bio-Plex protein array may be found at Bio-Rad Laboratories home page, www.bio-rad.com.

Additional teaching and information on Flow Cytometry process and the like and methods and related techniques, and Flow Cytometry and the like equipment, software, microspheres, beads and the like, may be found in U.S. Pat. No.: 6,592,822 issued to Chandler et al.; U.S. Pat. No. 5,981,180 issued to Chandler; U.S. Pat. No. 6,528,165 issued to Chandler et al.; U.S. Pat. No. 6,524,793 issued to Chandler; U.S. Pat. No. 6,514,295 issued to Chandler et al.; U.S. Pat. No. 6,449,562 issued to Chandler et al.; U.S. Pat. No. 6,411,904 issued to Chandler; U.S. Pat. No. 6,366,354 issued to Chandler; U.S. Pat. No. 6,268,222 issued to Chandler et al.; U.S. Pat. No. 6,139,800 issued to Chandler; U.S. Pat. No. 6,046,807 issued to Chandler; U.S. Pat. No. 5,736,330 issued to Fulton; and U.S. Pat. No. 6,057,107 issued to Fulton; U.S. Pat. No. 6,589,792 issued to Malachowski; U.S. Pat. No. 6,248,590 issued to Malachowski; U.S. Pat. No. 5,675,517 issued to Stokdijk; U.S. Pat. No. 6,225,046 issued to Vesey et al.; U.S. Pat. No. 6,549,275 issued to Cabuz et al.; U.S. Pat. No. 6,280,618 issued to Watkins et al.; and U.S. Pat. No. 6,382,228 issued to Cabuz et al.; and US Patent Application Publication No. US20020182609A1 in the name of Arcot.

Therefore, these more recent techniques allow for rapid detection of multiple molecules of interest, simultaneously, on small sample volumes, within an expedient format. Other forms of instrumentation that permits rapid throughput (greater than 50 samples/day) of experimental samples on small sample volumes (less than 50 uL sample volume), to determine multiple endpoints simultaneously (greater than 3), in a solution-based determination system would fall within the scope of our interests.

Endpoints can be grouped based on interest within the context of experimentation. Reference endpoints can be utilized to examine differences between sample acquisition between location upon a person, differences between people, changes based on a difference in time, and the like. Experimentally modified endpoints would be endpoints that change based on consumer product usage, a change in season, or any phenomena being examined experimentally.

Reference Endpoints are determined as follows: Samples can be analyzed for total protein, carbohydrate, sugar, lipid, fatty acid, RNA, DNA, or any other generalized class of constituents. These functional classes, such as total protein or a subset of protein such as generalized keratin, can then be used as references to index against specific measurements within the sample. An example would be measuring total protein then a specific keratin such as keratin 6. The clinical sampling process may not be consistent from sample to sample; therefore the total protein content of the sample can be used as a reference point to the quantitation of keratin 6 within the sample. Multiple samples from one clinical study can then be referenced to their specific total protein content, for accurate statistical comparison of keratin 6 between treatment conditions.

Experimentally Modified Endpoints—are determined as follows: First and foremost reference endpoints can be experimentally modified due to treatment or clinical condition. An example would be a clinical skin condition where more corneocytes slough at a higher rate, creating a higher total protein content for that clinical group or treatment when compared to a control group or treatment. Another example would be a lipid replenishing hand lotion; the increase in a reference lipid quantitation would be experimentally relevant to a comparison of hand lotion products. These simple examples are traditional and only a basis for more complex comparisons that will follow. Experimentally modified endpoints can and would be RNA production for specific modulations of tissues, and the production of biological markers. These markers could be proteins, lipids, carbohydrates, glycolipids, glycoproteins, GAGs, or any prokaryote or eukaryote product. These data forms can then be quantitated and examined as individual raw portions of information, but more importantly can be combined, indexed to pertinent reference endpoints, and/or consolidated into a data set for interpretation. Experimentally modified endpoints can also be referenced to other samples within one panelist.

Consumer Product

The methods of the present invention relate to the affect a product has on the epithelial tissue of a subject or the relative benefit of one product over another. In the first embodiment of the present invention the products are test product, whereas in the second embodiment of the present invention the products are test products or comparison products. Products may be any product which potentially may have an effect on epithelial tissue. Non-limiting examples of such products includes, personal cleansing products, such as but not limited to, cosmetics, hair colorants, body wash, shampoo, conditioner, makeup, lotions, topical lotions, ointments, creams, skin lotions and the like; personal care objects, such as but not limited to, tooth brushes, hair brush, brush for a pet, and the like; clothing, such as but not limited to underwear, footwear and the like; medicaments; pet food; toothpaste; mouth wash; hand sanitizers; disposable absorbent articles, such as but not limited to, pads, tampons, training pants, diapers; hard surface cleaning compositions; facial tissues; wet wipes, such as but not limited to baby wipes, facial wipes, and the like; cleaning compositions, such as but not limited to dishwashing detergent, bleach, laundry detergent and the like; and combinations thereof.

Typically, the test and comparison products are similar, such as two different brands of hand lotions, or two different brands of diapers, however, it is possible to compare different consumer products, such as comparing the effects on epithelial tissue of a diaper rash lotion to the effects on epithelial tissue of a diaper wearer.

Evaluating the Effect of the Product by Evaluating the Quantitative Changes

In general, if a consumer product were to be compared with a competing product or product upgrade for a desired consumer benefit the examiner could create a test of a comparison of the products. Prior to beginning the evaluation, each endpoint is established as a functional unit within a flow chart of data interpretation, such that relevant comparisons are already determined and specific claims are already concluded through a flow chart or map. These can be established in general or created specifically for an individual study. Endpoints can corroborate one another and can be coalesced into a functional group that in a flow diagram would be determined with "and" nomenclature. Some sample group comparisons can create pathway flow such as "if, then" statements as in comparing an experimental sample with a control. Taking the data at the conclusion of the study and proceeding through the defined flow diagram would then determine the benefit targets of the product.

Within this test, panelist could use different products over time, fill out questionnaires to communicate their product experiences, clinicians can assess panelists for clinical change to the panelists, and clinicians can then apply tapes to areas of the panelists where products were utilized. These samples would be transferred to a laboratory where technicians would perform extraction of the samples into a buffer, perform quantitative techniques and record endpoint quantities for each tape. The examiner would then collect the information from the consumers' questionnaires, clinical assessment, and laboratory quantitation and combine these data into a single form. The data set would then be queried for statistical differences, examined through the flow chart that assists in determining the relevance to the consumers desired product performance.

In both the first and second embodiments of the present invention once the marker analytes are identified, the evaluation of effect of the product is done by comparing the marker analytes from said affected areas with the marker analytes from said control area. In the first embodiment of the present invention this evaluation provides information on the effect of a test product on one or more effected surfaces. In the second embodiment this evaluation is done to provide comparative data between each of the one or more test products and each of the one or more comparison products, which is then compared to determine the relative benefits of the one or more test products and the one or more comparison products.

Article of Commerce

The present invention also includes article of commerce comprising informational indicia in association with said article of commerce. In one optional embodiment of the present invention the informational indicia comprises information on the relative benefits of one or more consumer products and one or more comparison products. The information is determined according to the methods of the present invention. In another optional embodiment of the present invention the informational indicia comprises at least one assertion about at least one effect that a consumer product has on the status of an affected area of epithelial tissue when a consumer product is applied to the affected area of epithelial tissue.

The phrase "in association with" means the informational indicia are in some fashion present on and/or in or are in some fashion connected, such as physically or via some form of mental association, with the article of commerce to be able to communicate the information therein. Examples of this may include, but are not limited to either directly printed on the article of commerce itself or presented in a different manner including, but not limited to, a brochure, print advertisement, electronic advertisement, and/or verbal communication, so as to communicate the information therein. The exact form this association of the article of commerce with the informational indicia will depend upon may factors, such as what the article of commerce is, the nature and form of the informational indicia, the information contained in the informational indicia etc. In one optional embodiment of the present invention the informational indicia comprises some assertion and/or information about the article of commerce, e.g., if the article of commerce is a package of diapers, the informational indicia may contain some assertions about the effect the diapers in the package has on an affected epithelial tissue, or it may contain some information about the benefits of the diapers in the package compared to a competitors diapers, provided that the information has been obtained by the methods of the present invention. It is to be understood that when the informational indicia comprises some assertion and/or information about the article of commerce, that article of commerce is not to be limited to diapers, but may include any article of commerce which may potentially interact with epithelial tissue, and non limiting examples of these types of products are described herein.

In another alternative embodiment the informational indicia comprises some assertion and/or information about a product, which is not the article of commerce. In this optional embodiment the article of commerce may be advertisements, such as print, radio, television and/or advertisements placed on any other similar electronic media. Specific examples of this would include, advertisements in magazines, newspapers and the like containing some information about a consumer product, or assertions based on information obtained by the methods of the present invention. Alternatively, the article of commerce may be magazines, newspapers and the like with the informational indicia contained in some fashion in the magazines, newspapers and the like, such as an article, editorial, advertisement, supplement, detachable insert and the like and combinations thereof. It is also within the scope of the present invention that the informational indicia be or be contained in pamphlet, such as but not limited to those sent to hospitals, pediatricians and primary care physicians that provide data demonstrating the benefits of a product. Likewise the article of commerce comprising the informational indicia may be present in various types of electronic media. One non-limiting example is web page or web pages, containing the informational indicia. Another non-limiting example are television or radio advertisements, such as but not limited to infomercials (either radio or television), conventional advertisements, and the like and combinations thereof. The informational indicia may also be supplied as part of a program supplied on electronic media, such as sponsorship a program on television and the sponsorship information comprises the informational indicia. Alternatively, the informational indicia is included as part of the program content, such as in a product review on a talk show, use of a product by a character in a program and the character then supplies the appropriate informational indicia, such as in the form of dialogue. Another alternative, would be placement of a product in a "reality" television program, and either provide the informational indicia via the participants or provide the informational indicia via another related means which is associated with the "reality" television program.

EXAMPLES

Example 1

Evaluation of Quantitative Changes on One or More Affected Surfaces of Epithelial Tissue of an Animal Subject of an Animal Subject Caused by a Test Product In example 1 the test product is a baby wipe which comprises a lotion reliably contained on a nonwoven substrate. The lotion, or composition is detailed below in Table I. The nonwoven substrate is a 60/40 polyethylene/rayon hydroentangled nonwoven material available from J.W. Suominen Company of Finland having a basis weight of about 58 grams per square meter. The control product is a cotton washcloth that is wet with tap water.

TABLE I

| Ingredient | Percent of composition w/w [g] |
| --- | --- |
| Disodium EDTA | 0.1 |
| Sodium Dihydrogenphosphate dihydrate | 0.4 |
| Aloe Barbadensis | 0.0025 |
| Acrylates/Vinyl Isodecanoate Crosspolymer | 0.25 |
| Dimethicone | 3.0 |
| Preservative system* | 2.25 |
| Sorbitan Oleate | 0.2 |
| Sodium Hydroxide 32% solution (q.s. to pH 5.5) | 0.12 |
| Water | Quantity sufficient to 100% |

*a mixture of Methylparaben, Propylparaben, Eethylparaben, Benzyl Alcohol, Propylene Glycol For one week size 3 Pampers® diapers were applied to suitable sized babies of various genders. For the same week these children use the same products for cleaning. The cleaning product is then changed to either the, product or control. The same type of diapers is used during the test as was in the one week before the test, namely size 3 Pampers® diapers.

After 4 days using product or control, erythema is assessed by an expert skin grader based on the grading scale below. The overall surface covered by the diaper is graded and give a score of 0-4 based on the grading scale below. Additionally, individual scores of 0-4 are also given for the left buttock, front left waist, genital, left hip, left intertrigenous and left perianal for every child. The mean values for each of these scores is then obtained and recorded. See FIG. 1

Erythema Scale

0 No apparent cutaneous involvement.

½ Greater than 0, less than 1.

1 Faint but definite erythema, no eruptions or broken skin or no erythema but definite dryness; may have epidermal fissuring.

1½ Greater than 1, less than 2.

2 Moderate erythema, may have a few papules or deep fissures, moderate-to-severe erythema in the cracks.

2½ Greater than 2, less than 3.

3 Severe erythema (beet redness), may have generalized papules or moderate-to-severe erythema with slight edema (edges well defined by raising).

3½ Greater than 3, less than 4.

4 Generalized vesicles or eschar formations or moderate-to-severe erythema and/or edema extending beyond the area of the patch.

Subsequent to the grading each of the left buttock, front left waist, genital, left hip, left intertrigenous and left perianal locations are harvested. The harvesting is done by application of D-squame® tape to each of these locations, removal of the tape and then placing each of the tapes into individual labeled glass vials. Six D-squame® tapes are used per child. These glass vials may be extracted immediately or they may be stored for later extraction by storing the samples at −70° C. In any event any extraction procedure is performed at about 23° C.

To each vial containing D-squame® tape 1 mL of harvesting solution is added. The harvesting solution contains phosphate buffered saline with 0.2% sodium dodecyl sulphate, and 1% propylene glycol. Each vial containing harvesting solution and D-squame® tape are then subjected to sonication for about thirty minutes. The sonication occurs in a Bransonic B300 sonicating water bath which is filled with ice-water, and has a frequency of about 34 kHz and a power of about 50 watts. These glass vials may be analyzed immediately or they may be stored for later analysis by storing the samples at −70° C. In any event, any analysis procedure is performed at about 23° C.

The following analysis is performed on the solutions in each vial:
1. An 100 uL aliquot from each sample is analyzed using the Pierce Micro BCA total Protein Assay kit Catalog #23235 following kit instructions for microwell plate protocol. (Pierce, 3747 N. Meridian Road P.O. Box 117, Rockford Ill. 61105). This assay was analyzed on a Molecular Devices Spectramax spectrophotometer available from Molecular Devices Corporation 1311 Orleans Drive Sunnyvale, Calif. 94089;
2. A 25 uL aliquot from each sample is analyzed using the Human SkinMAP LINCOplex KIT, beads target keratins 1&10, Keratin 6, and Involucrin. (Linco Research 14 Research Park Drive, St. Charles Mo. 63304) This kit was analyzed on a BioRad BioPlex protein array system available from Bio-Rad Laboratories 2000 Alfred Nobel Drive Hercules, Calif. 94547; and
3. A 100 uL aliquot is analyzed for ATP content using the Promega Cat# G7571, adding 100 uL of luciferase working reagent to each sample within an assay plate, incubating 2 min. then recording the luminescence using a Tecan Ultra 384. (Promega Corporation, 2800 Woods Hollow Road, Madison Wis. 53711).

The data from each of these three tests is complied, and the relevant means calculated to arrive at a mean score of analyte content for each of the sampled locations. These means are tabulated and graphed. See FIGS. 1 to 12. These means are then combined with the expert grader erythema scores and statistically analyzed.

Turning now to the tabulated data, examining the erythema score it can be seen there is no statistical difference between the product and control, FIGS. 1 and 2.

However, the subsequent detailed analysis presents a different picture.

The BCA total protein recovered indicates that there was a reduction in the amount of protein harvested from children using the product over those using the control. See FIGS. 3 and 4. The second analysis above, is a concurrent multiple analyte profiling for skin endpoints. The keratins 1&10, which indicate corneocyte organization and content, were reduced in the buttock location over the control. See FIGS. 5 and 6. Keratin 6, which is a marker of chronic irritation and wound recovery, were significantly reduced in the buttocks, genital, and perianal locations, over the control. See FIGS. 7 and 8. Invoulcrin, which is a marker of corneocyte organization and a marker of the thickness of the stratum corneum, was significantly reduced in the buttocks, intertrigenous, and perianal locations, over the control. See FIGS. 9 and 10.

Lastly, the ATP content, which is a marker of skin surface microflora and BM contamination, was similar between product and control. See FIGS. 11 & 12.

When examining the data set as a whole a clear difference between the product and control can be seen. The product is better than the control as the skin is less chronically irritated (keratin 6 FIGS. 7 and 8), is more organized and has a more robust barrier (BCA total protein FIGS. 1 and 2, keratins 1&10 FIGS., 3 and 4 and involucrin FIGS. 9 and 10), and is similar in cleaning ability to a cotton wash cloth (ATP FIGS. 11 and 12).

Example 2

A magazine advertisement containing informational indicia which comprises the assertion that the test product of Example 1 when applied to an affected area of epithelial tissue reduces diaper rash.

Example 3

A television advertisement containing informational indicia which comprises the assertion that the product of Example 1 when applied to an affected area of epithelial tissue reduces diaper rash.

Example 4

A baby wipe comprising the product of Example 1 containing informational indicia in association therewith which comprises the assertion that the baby wipe when applied to an affected area of epithelial tissue reduces diaper rash.

Example 5

Determination of the Relative Benefits of Consumer Products

Twenty-three panelists are given two different body lotion products. Each consumer was provided with an identical cleansing product, such as Olay® Sensitive Skin Bar Soap, and instructed to use this for the duration of the test in place of their normal skin cleansing and bathing products. The panelists' dorsal forearm hair is clipped and baseline D-squame® tapes are applied to each dorsal forearm. Each tape is placed into a glass vial. This is then frozen dry, stored and assessed after the conclusion of the study to provide an accurate baseline result.

The two products being compared product's A and B are detailed in table II below. In product A the Tretinoin is separate from the rest of the formulation and applied prior to the application of the remainder of the product.

TABLE II

| Ingredient | Product A Wt/Wt % | Product B Wt/Wt % |
| --- | --- | --- |
| Water, purified | Quantity sufficient to 100 | Quantity sufficient to 100 |
| Glycerin, USP | 3.0 | 3.0 |

TABLE II-continued

| Ingredient | Product A Wt/Wt % | Product B Wt/Wt % |
| --- | --- | --- |
| Cetyl Palmitate | 3.0 | 3.0 |
| Mineral Oil, USP | 2.0 | 2.0 |
| Petrolatum, USP | 1.85 | 1.85 |
| Cetyl Alcohol, NF | 1.26 | 1.26 |
| Glyceryl Hydroxystearate | 0.74 | 0.74 |
| Stearic Acid | 0.55 | 0.55 |
| Steareth-100 | 0.5 | 0.5 |
| Dimethicone | 0.3 | 0.3 |
| Octyldodecyl Myristate | 0.3 | 0.3 |
| Potassium Hydroxide, NF | 0.125 | 0.125 |
| DMDM Hydantoin and Idopropynyl Butylcarbamate | 0.1 | 0.1 |
| Tetrasodium EDTA | 0.1 | 0.1 |
| Acrylates/C10–30 Alkyl Acrylate Crosspolymer | 0.075 | 0.075 |
| Carbomer 951 | 0.05 | 0.05 |
| Tretinoin | 0.025 | — |

Each product is applied to the dorsal forearm by the opposite hand by the panelists after morning bathing habits each day for a total four weeks. Panelists' apply each test product twice a day for a period of four weeks.

At weeks 1, 2, and 4 weeks during the treatment period panelists' have 6 tapes recovered from the dorsal forearm. These 6 D-squame® tapes are employed in a serial fashion in one location on each dorsal forearm for a total of six D-Squame® tapes. Each tape placed into its own labeled vial. On days that D-squame® tapes were removed from the surface, panelists were told to delay application of test products until after morning clinical evaluation. Different locations within the dorsal forearm were randomly utilized for different time points, that is week 1, 2, and 4 within the study. The second, fourth and sixth tapes from each of the sample weeks are analyzed, as described herein, and the results for each week are used to calculate mean values for each analyte content for each week. These means are tabulated and graphed. See FIGS. 13 to 18.

These glass vials may be analyzed immediately or they may be stored for later analysis by storing the samples at −70° C. In any event, any analysis procedure is performed at about 23° C.

To each vial containing D-squame® tape 1 mL of harvesting solution is added. The harvesting solution contains phosphate buffered saline with 0.2% sodium dodecyl sulphate, and 1% propylene glycol. Each vial containing harvesting solution and D-squame® tape are then subjected to sonication for about thirty minutes. The sonication occurs in a Bransonic B300 sonicating water bath which is filled with ice-water and has a frequency of about 34 kHz and a power of about 50 watts. These glass vials may be analyzed immediately or they may be stored for later analysis by storing the samples at −70° C. In any event any analysis procedure is performed at about 23° C.

Figure 16:
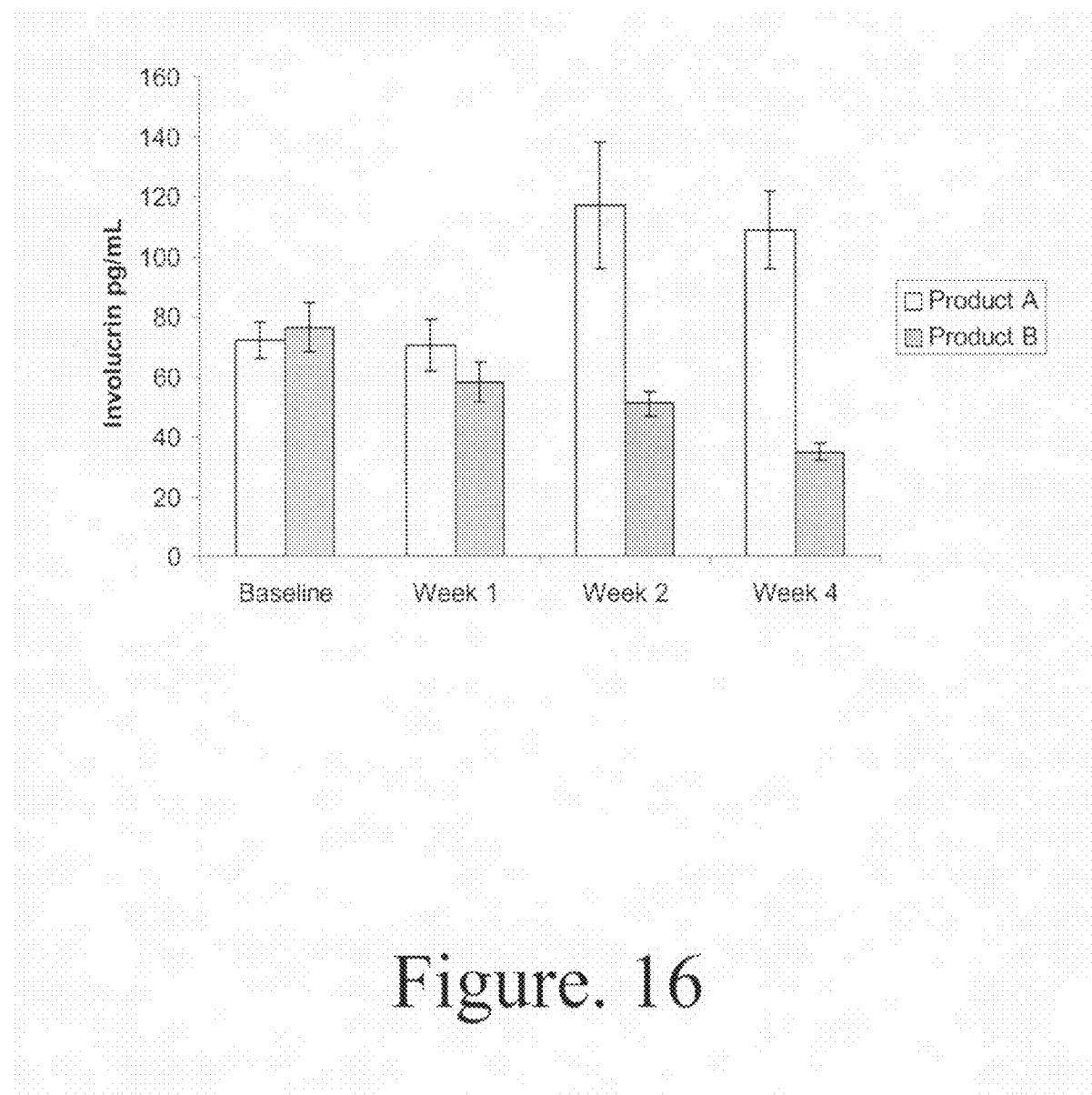
FIG. 16 is a bar graph illustrating Bead assay for Involucrin mean of tapes 2, 4, and 6 for each product and each time according to example 5.
Figure 17:
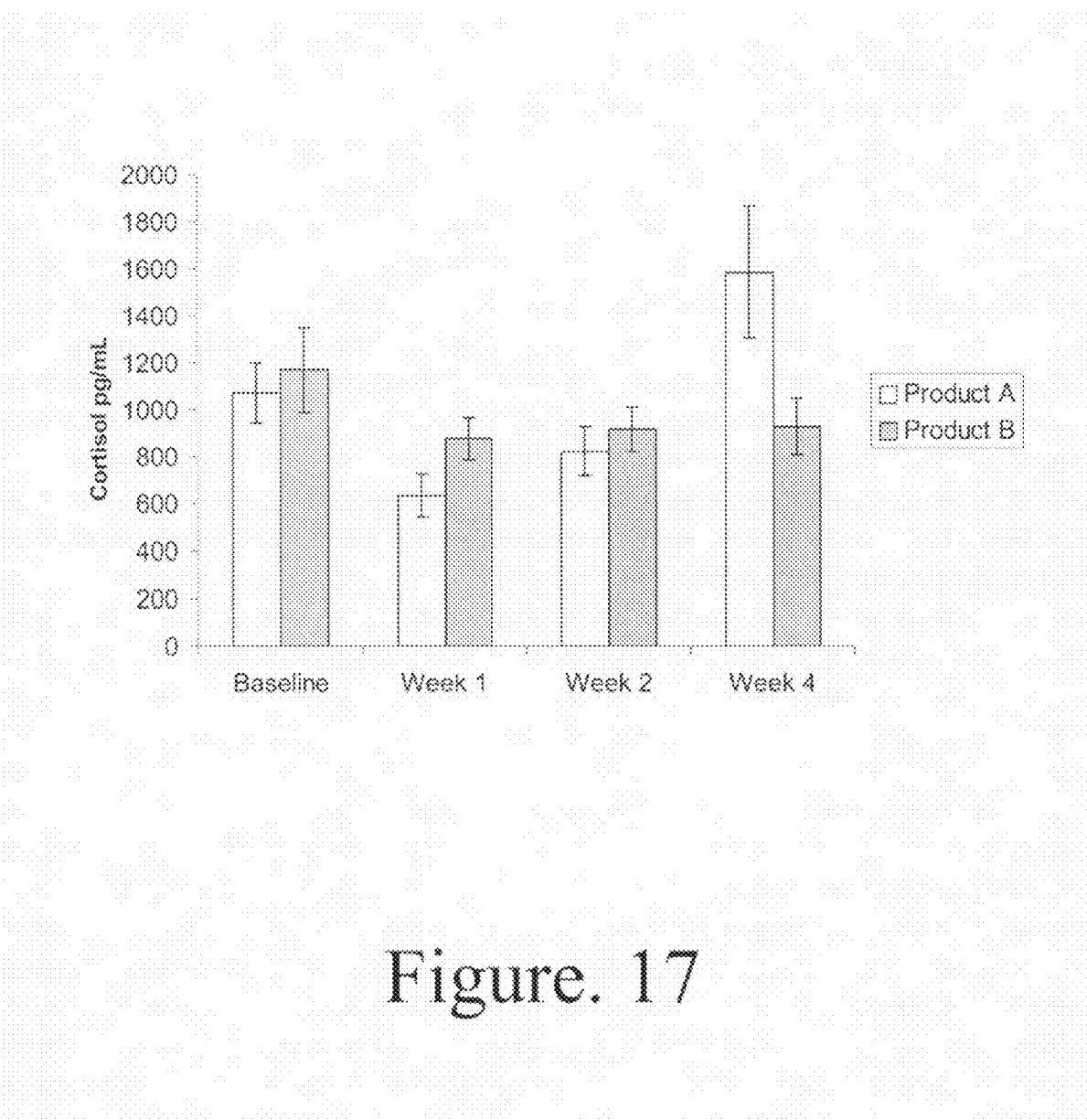
FIG. 17 is a bar graph illustrating Bead assay for Cortisol mean of tapes 2, 4, and 6 for each product and each time according to example 5

The following analysis is performed on the solutions in each vial:

1. An 100 uL aliquot from each sample is analyzed using the Pierce Micro BCA total Protein Assay kit Catalog #23235 following kit instructions for microwell plate protocol. (Pierce, 3747 N. Meridian Road P.O. Box 117, Rockford Ill. 61105). This assay was analyzed on a Molecular Devices Spectramax spectrophotometer available from Molecular Devices Corporation 1311 Orleans Drive Sunnyvale, Calif. 94089;

2. A 25 uL aliquot from each sample is analyzed using the Human SkinMAP LINCOplex KIT, beads target keratin 1&10, Keratin 6, cortisol, and Involucrin. (Linco Research 14 Research Park Drive, St. Charles Mo. 63304) This kit was analyzed on a BioRad BioPlex protein array system available from Bio-Rad Laboratories 2000 Alfred Nobel Drive Hercules, Calif. 94547; and Statistical analysis demonstrates a significant difference in the quantity of keratins 1&10 and keratin 6 at week four with product B being lower than product A. The keratins 1&10 reduction indicates a stratum corneum that is more structurally organized, the reduction in keratin 6 in product B indicates a reduction in chronic irritation of the epidermis and a reduction in wound repair mechanisms. Involucrin is significantly higher for product A as early as one week of use (FIGS. 16 and 18) indicating a thinner stratum corneum on the epidermis for product A use. Cortisol, a systemic growth factor, is varied significantly within product A usage (FIGS. 17 and 18). A significant reduction in cortisol from product A usage in comparison to product B within the first week of usage (FIGS. 17 and 18) indicates an increase in cellular activity, potentially an increase in cellular division, one of the mechanisms of cortisol. A significant increase in cortisol levels for product A by week four (FIGS. 17 and 18) may be indicative of increased vascular activity or an increase in trans-epidermal water loss due to the indicated reduction in stratum corneum barrier seen in the involucrin data (FIGS. 16 and 18).

Taken as a whole the data sets for product A would indicate a product composition that would be ideal for consumers whom possess skin with excess stratum corneum corneocytes (increases in involucrin), are older and are interested in increasing cell-turnover rates (uptake of cortisol). Product B would be a composition for sensitive skin in that it increases the barrier properties of the skin (decrease in surface keratins 1&10, decrease in surface involucrin: therefore irritants less apt to penetrate), reduces irritation (decreases keratin 6) and is an epidermal stress-free product (monotone cortisol levels).

Each product composition could be produced for specific consumer targets and provide completely different product claim sets for efficacy.

Example 6

A magazine advertisement containing informational indicia which comprises information on the relative benefits of product A of Example 5 on anti-aging effects over product B of Example 5.

Example 7

A television advertisement containing informational indicia which comprises information on the relative benefits of product A of Example 5 on anti-aging effects over product B of Example 5.

Example 8

A skin lotion comprising product B of Example 5 containing informational indicia in association therewith which comprises information on the relative benefits of product B with respect to sensitive skin over Product A of Example 5.

The dimensions and values disclosed herein are not to be understood as being strictly limited to the exact numerical values recited. Instead, unless otherwise specified, each such dimension is intended to mean both the recited value and a functionally equivalent range surrounding that value. For example, a dimension disclosed as "40 mm" is intended to mean "about 40 mm."

All documents cited in the Detailed Description of the Invention are, in relevant part, incorporated herein by reference; the citation of any document is not to be construed as an admission that it is prior art with respect to the present invention. To the extent that any meaning or definition of a term in this document conflicts with any meaning or definition of the same term in a document incorporated by reference, the meaning or definition assigned to that term in this document shall govern.

While particular embodiments of the present invention have been illustrated and described, it would be obvious to those skilled in the art that various other changes and modifications can be made without departing from the spirit and scope of the invention. It is therefore intended to cover in the appended claims all such changes and modifications that are within the scope of this invention.

What is claimed is:

1. A method for evaluating quantitative changes on one or more affected surfaces of epithelial tissue of an animal subject for stress on said epithelial tissue caused by a test product, comprising the steps of:
   (a) harvesting one or more control surfaces of epithelial tissue from said animal subject to collect a first portion of mixed analytes as a control sample;
   (b) harvesting said affected surface of epithelial tissue from said animal subject of step (a) to collect a second portion of mixed analytes as a test sample;
   (c) identifying a marker analyte selected from at least one of fibronectin, inositol containing compounds, cortisol, S100, calcium binding proteins, plectin, profilin, SPRR1, keratin 6, lipids and sweat, in said test and control samples;
   (d) evaluating the effect of said test product on the epithelial tissue by evaluating said quantitative changes on said affected areas of the epithelial tissue by comparing the marker analyte from said affected areas with the marker analyte from said control area.

2. The method of claim 1 wherein said marker analytes in said test and control samples are identified using antibody probes for said marker analytes.

3. The method of claim 1 wherein said harvesting of said control sample and said test sample are a procedure selected from the group consisting of application of tape, rinsing by lavage method, biopsy, swabbing, scraping, blotting and combinations thereof.

4. The method of claim 1 wherein said test product is selected from the group consisting of cosmetics, hair colorants, body wash, shampoo, conditioner, makeup, lotions, topical lotions, ointments, creams, skin lotions and combinations thereof.

5. The method of claim 1 wherein said test product is selected from the group consisting of toothbrushes, hairbrushes, pet brushes, and combinations thereof.

6. The method of claim 1 wherein said test product is selected from the group consisting of underwear, footwear, and combinations thereof.

7. The method of claim 1 wherein said test product is medicaments.

8. The method of claim 1 wherein said test product is pet food.

9. The method of claim 1 wherein said test product is selected from the group consisting of toothpaste, mouth wash and combinations thereof.

10. The method of claim 1 wherein said test product is selected from the group consisting of pads, tampons, training pants, diapers and combinations thereof.

11. The method of claim 1 wherein said test product is selected from the group consisting of facial tissues, wet wipes and combinations thereof.

12. The method of claim 1 wherein said test product is selected from the group consisting of hard surface cleansing compositions, dishwashing detergent, bleach, laundry detergent and combinations thereof.

* * * * *